United States Patent [19]
Kirby et al.

[11] Patent Number: 6,046,764
[45] Date of Patent: Apr. 4, 2000

[54] VISUAL INSPECTION SYSTEM OF MOVING STRIP EDGES USING CAMERAS AND A COMPUTER

[75] Inventors: George J. Kirby, Newton; Jon F. Ewing, Reading; Arthur B. Borgeson, Hanson, all of Mass.

[73] Assignee: The Gillette Company, Boston, Mass.

[21] Appl. No.: 08/927,301

[22] Filed: Sep. 11, 1997

Related U.S. Application Data

[63] Continuation of application No. 08/452,647, May 25, 1995, abandoned.

[51] Int. Cl.[7] .................................................. H04N 7/18
[52] U.S. Cl. ............................................ 348/92; 348/128
[58] Field of Search ................................ 348/86, 88, 91, 348/92, 125, 128, 131, 142, 143, 159, 89; 73/104, 105; 324/750; 356/69; 396/19; H04N 7/18

[56] References Cited

U.S. PATENT DOCUMENTS

| Re. 33,357 | 9/1990 | Randall ..................................... 348/89 |
| 2,027,595 | 1/1936 | Knobel et al. ............................ 209/111 |
| 2,065,713 | 12/1936 | Knobel et al. .............................. 88/14 |
| 2,185,010 | 12/1939 | Young ......................................... 88/14 |
| 2,502,503 | 4/1950 | Berkley ....................................... 88/14 |
| 2,735,329 | 2/1956 | Meunier ...................................... 88/14 |
| 3,025,747 | 3/1962 | Casselman et al. ........................ 88/14 |
| 3,655,989 | 4/1972 | Robinson ......................... 250/219 WD |
| 3,953,186 | 4/1976 | Howey ........................................ 65/51 |
| 4,240,110 | 12/1980 | Henry ........................................ 348/88 |
| 4,247,204 | 1/1981 | Merlen et al. ............................ 356/431 |
| 4,372,658 | 2/1983 | O'Connor et al. ........................ 396/19 |
| 4,583,854 | 4/1986 | Lozar ....................................... 356/237 |
| 4,665,317 | 5/1987 | Ferriere et al. .......................... 348/128 |
| 4,705,957 | 11/1987 | Puffer et al. ............................. 250/568 |
| 4,728,800 | 3/1988 | Surka ....................................... 250/572 |
| 4,853,776 | 8/1989 | Itaya et al. ................................ 348/88 |
| 4,972,494 | 11/1990 | White et al. .............................. 348/92 |
| 5,085,232 | 2/1992 | Maguire et al. ......................... 250/572 |
| 5,182,457 | 1/1993 | Hagmann ................................. 250/572 |
| 5,197,012 | 3/1993 | El-Sarout ................................ 364/470 |
| 5,220,178 | 6/1993 | Dreiling et al. ......................... 250/572 |
| 5,239,376 | 8/1993 | Dittmann et al. ......................... 348/88 |
| 5,243,408 | 9/1993 | Whitman, III .......................... 356/430 |
| 5,305,894 | 4/1994 | McGarvey ................................ 348/89 |
| 5,394,183 | 2/1995 | Hyslop ..................................... 348/88 |
| 5,440,648 | 8/1995 | Roberts et al. ......................... 348/133 |
| 5,475,316 | 12/1995 | Hurley et al. ........................... 324/750 |

FOREIGN PATENT DOCUMENTS

| 38 34 052 A1 | 4/1990 | Germany . |
| 39 26 349 A1 | 2/1991 | Germany . |

OTHER PUBLICATIONS

PCT/US96/07656, International Search Report, May 5, 1996.

Primary Examiner—Young Lee
Attorney, Agent, or Firm—Fish & Richardson P.C.

[57] ABSTRACT

A continuous edge of a strip of material is processed as it moves in a direction along the length of the strip. The condition of the continuous edge of the moving strip is inspected after it has been processed. The strip is cut into pieces. And the pieces are sorted into groups in response to the condition of the edge. The edge is continuously monitored by a pair of parallel, closely spaced laser beams. A visualization system includes a camera, a monitor, and a storage systems. The camera images an edge of the moving strip of material. The monitor, coupled to the camera, displays images captured by the camera. The storage system, coupled to the camera and the monitor, stores images captured by the camera. The monitor is capable of displaying the stored images.

8 Claims, 20 Drawing Sheets

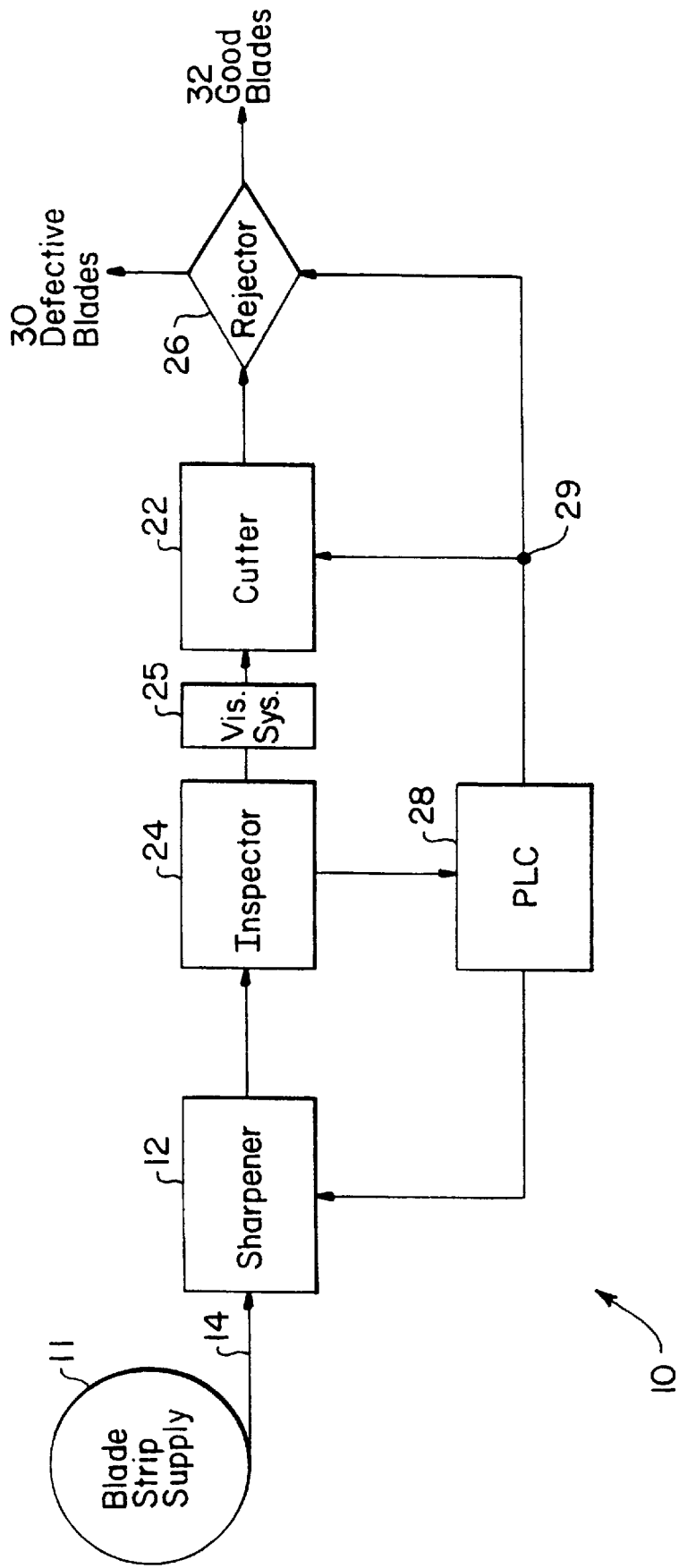

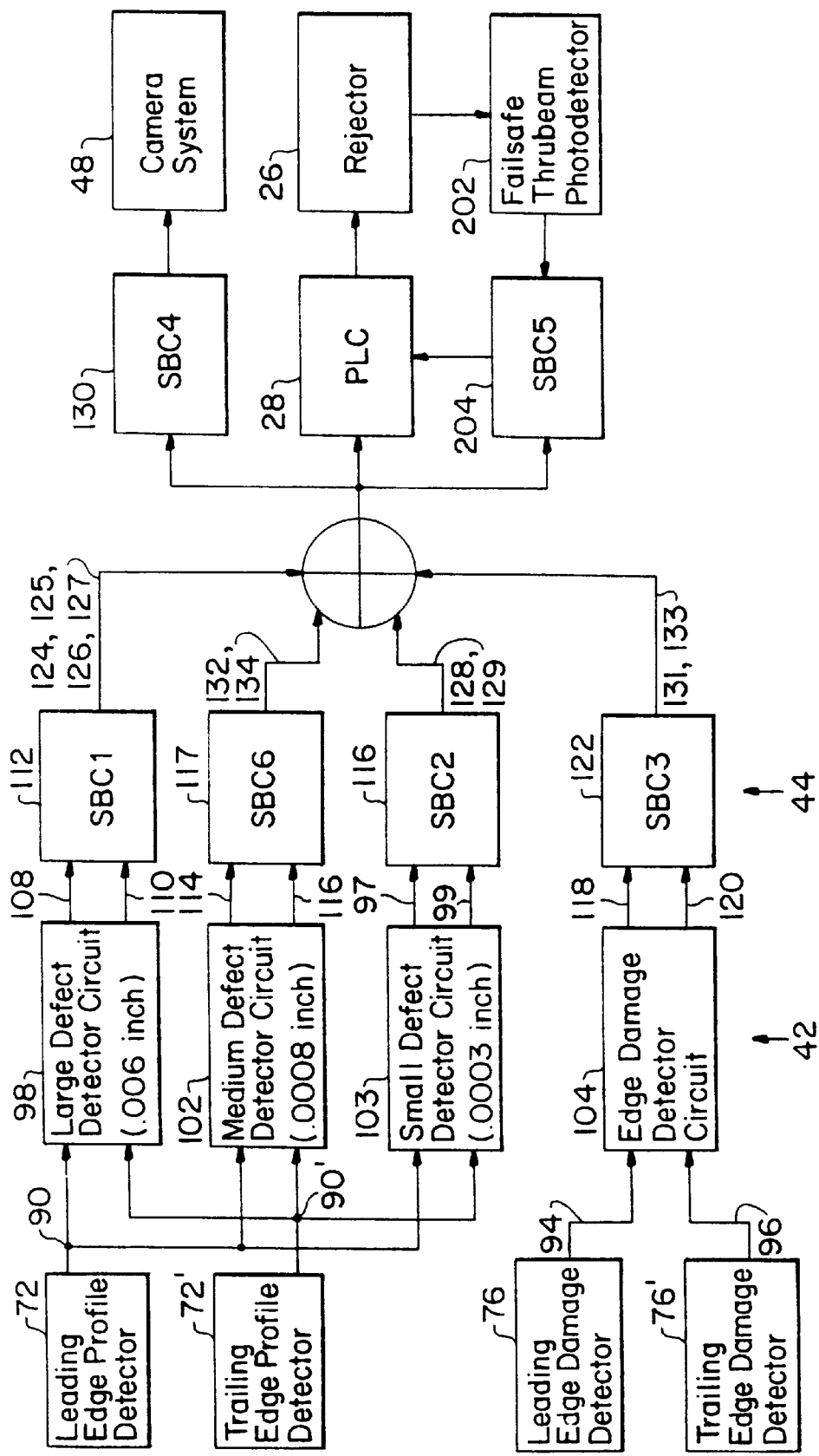

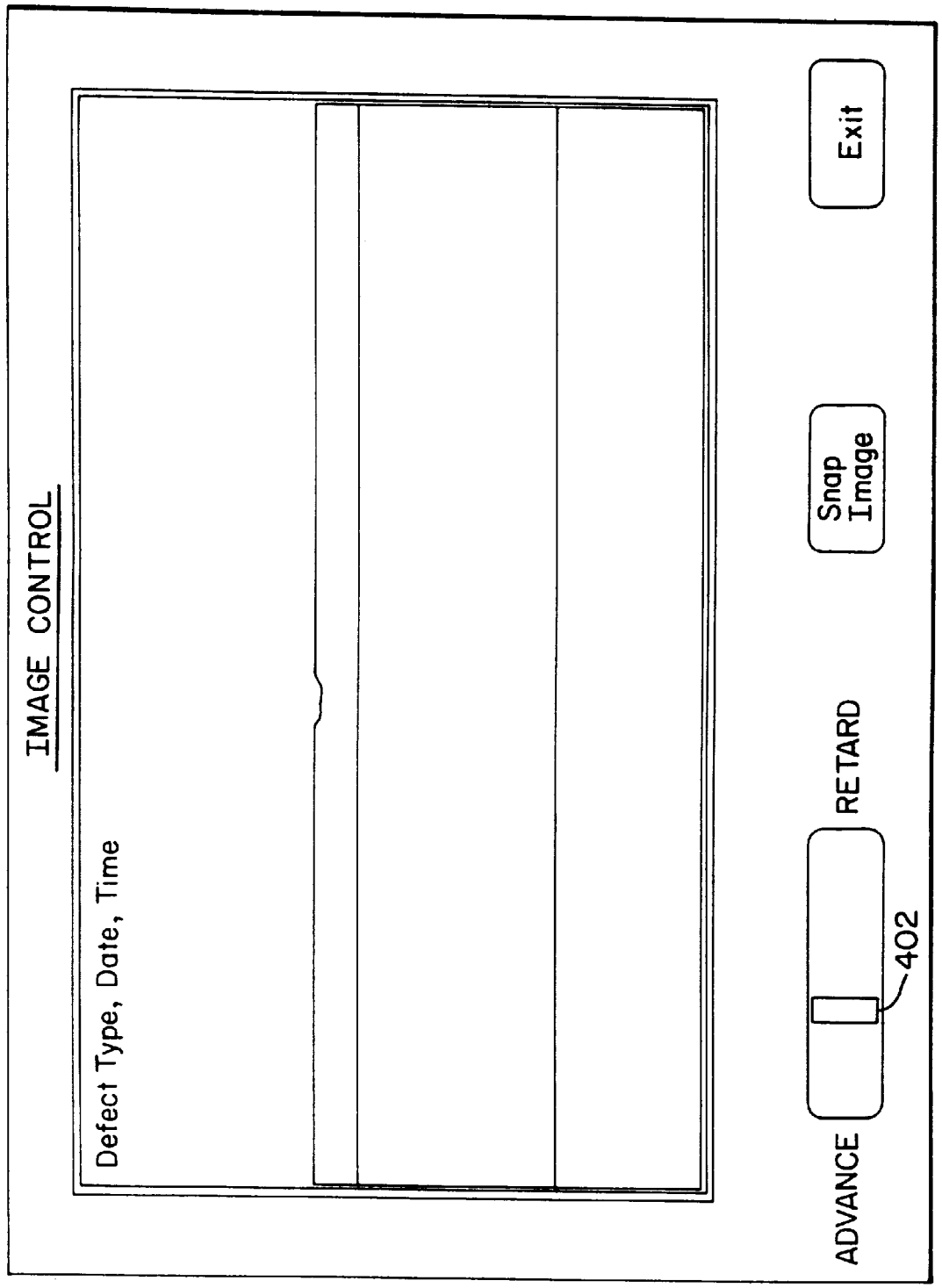

VISUAL INSPECTION SYSTEM OF MOVING STRIP EDGES USING CAMERAS AND A COMPUTER

This is a continuation of application Ser. No. 08/452,647, filed May 25, 1995, now abandoned.

BACKGROUND OF THE INVENTION

This invention relates to inspection of edges.

The sharpened edges of razor blades, for example, are typically inspected after the blades have been cut from a strip of steel that has been passed through a sharpening machine. An operator transfers the razor blades to spindles to form a block of blades with the sharpened edges of the blades all facing in the same direction. Defects are detected by holding the block of blades with the sharpened edges at different angles with respect to a light source and looking for stray reflections of light that indicate damaged blades.

To remove a defective blade from the block of blades the operator transfers a section of good blades from the block onto another set of spindles and removes and discards several blades from the block in the vicinity of the reflection. The operator then transfers the good blades back onto the original spindles and again checks for defects.

SUMMARY OF THE INVENTION

In general, in one aspect, the invention features a method including processing a continuous edge of a strip of material which is moving in a direction along the length of the strip. The condition of the continuous edge of the moving strip is inspected after it has been processed. The strip is cut into pieces. And the pieces are sorted into groups in response to the condition of the edge.

Implementations of the invention may include one or more of the following features. The method may be used with a manufacturing line that makes razor blades, where the strip of material is a strip of razor blade material and the pieces are razor blades. The razor blades may be sorted into a first group of good razor blades and a second group of defective razor blades based on the detection of edge defects. The inspector may include a first laser system having a first projector for projecting a first laser beam at the cutting edge in a direction perpendicular to the direction of movement of the strip and perpendicular to the cutting edge and a first profile detector for detecting a portion of the first laser beam passing over the cutting edge and for generating a first signal representing the detected portion of the first laser beam. Another detector can receive reflected light from the edge for detecting edge damage. There may also be a second laser system, in close proximity to the first laser system, including a second projector, for projecting a second laser beam at the cutting edge in a direction perpendicular to the direction of movement of the strip and perpendicular to the cutting edge and a second profile detector for detecting a portion of the second laser beam passing over the cutting edge and for generating a second signal representing the detected portion of the second laser beam. A normalizing circuit may receive the first and second signals from the first and second profile detectors. Artifacts associated with movement of the cutting edge may be filtered out. An edge discontinuity signal may be generated and processed to detect defects in the cutting edge. And a defect signal may be generated in response to detected defects. The defect detection circuit may detect defects by detecting corresponding peaks of opposite polarity within a predetermined amount of time in the edge discontinuity signal. The predetermined amount of time may be dependent upon the speed with which the strip is moving and the distance between the first and second laser beams.

In general, in another aspect, the invention features a manufacturing line including a machine that processes a continuous edge of a strip of material; an inspector that determines the condition of the edge; a cutter that cuts the strip into pieces; and a sorter that sorts the pieces into at least two groups in response to the condition of the edge.

In general, in another aspect, the invention features an apparatus for continuously monitoring an edge of a strip of material, the apparatus having a pair of parallel, closely spaced laser beams, e.g., as described above.

In general, in another aspect, the invention features a visualization system including a camera, a monitor, and a storage system. The camera images an edge of a moving strip of material, the monitor, coupled to the camera, displays images captured by the camera. The storage system, coupled to the camera and the monitor, stores images captured by the camera. The monitor is capable of displaying the stored images.

Implementations of the invention may include one or more of the following features. A light source may be directed at the edge of the strip. A first camera and lens, in close proximity to the light source and on a first side of the strip, may take pictures of the edge of the strip. A second camera and lens, may be in close proximity to the light source and on a second side of the strip, and may take pictures of the edge of the strip. Strobe illumination may be used to stop motion for the images. A computer that receives pictures from the first and second cameras, may generate digitized images of the pictures, and may display the digitized images on a monitor. Pictures may be acquired on the computer at the operator's discretion, or, when the computer receives a defect signal, the cameras may take pictures of the strip at a predetermined time such that pictures are taken of detected defects. The predetermined time may be adjustable and the computer may include an input device through which an operator can input timing adjustments. A storage system may store the digitized images in response to instructions from the computer, and an operator using an input device of the computer may cause the computer to retrieve stored digitized images from the storage system for display on the monitor.

The invention may include one or more of the following advantages. Edge defects may be rapidly and accurately detected and defective pieces rejected. The operator may observe images of the defects and of the edge and view statistical information about defects.

Other advantages and features will become apparent from the following description and from the claims.

BRIEF DESCRIPTION OF THE DRAWINGS

FIG. 1 shows a block diagram of a razor blade manufacturing line;

FIG. 9 shows a block diagram of the controls for the detection and rejection elements of an inspection system;

FIG. 17 shows an image control screen;

DESCRIPTION OF THE PREFERRED EMBODIMENTS

Razor Blade Manufacturing Line

Figure 2A:
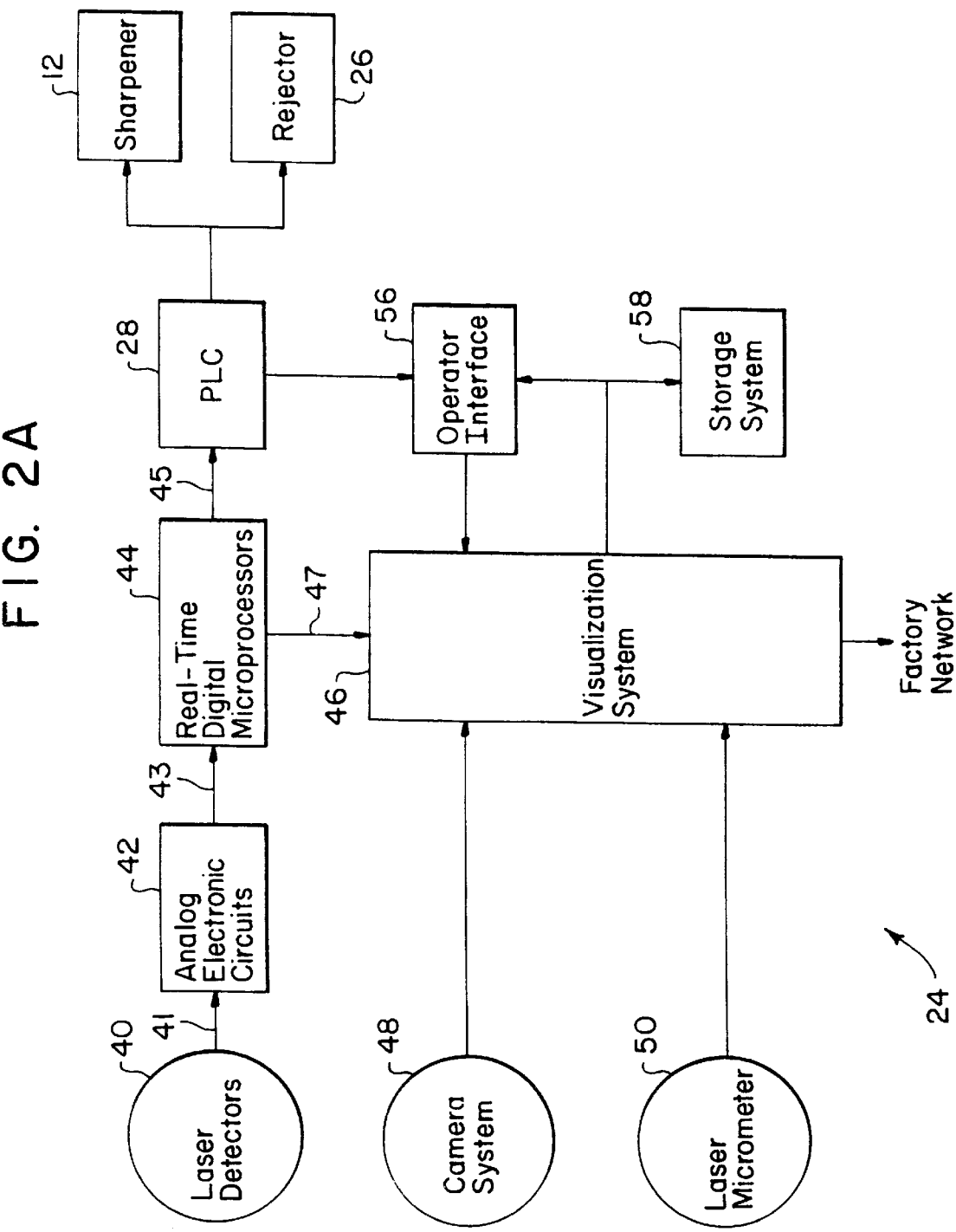
FIG. 2A shows a block diagram of an inspection system.

Referring to FIG. 1, a manufacturing line 10 makes razor blades by passing continuous steel strip 14 from a supply coil 11 through a sharpener 12 that grinds and polishes the strip 14. Before being cut into individual razor blades by a cutter 22, the strip is examined at an inspector 24.

Inspector 24 detects edge defects in the sharpened edge of the strip. Depending upon the sensitivity of the inspector, different types of edge defects may be detected. Among the defects detected are those which interrupt (cause gaps in) the continuous sharp edge of the steel strip passing through the inspector.

Inspector 24 sends defect information to a programmable logic controller (PLC) 28, a visualization system 46, and a rejector 26. PLC 28 dynamically controls the operation of rejector 26. With information provided by inspector 24 and by other line 10 equipment, PLC 28 causes rejector 26 to discard defective razor blades 30 and provide defect-free razor blades 32 as a finished product of line 10.

PLC 28 also maintains counts of the number of good razor blades produced and the number of defective razor blades discarded. The counts can be used by the PLC to detect when process limit thresholds are met and stop the machine for excessive defective product. If on the other hand, no blades are detected as defective in a large amount of good product, the detection system may have ceased functioning. The PLC will stop the machine for a detector "failsafe."

Inspection

Referring to FIG. 2A, inspector 24 includes laser detectors 40 which continuously monitor the edge of strip 14 and send signals 41 to high speed analog electronic circuit 42. Analog electronic circuit 42 processes the received signals 41 to detect defects in the edge and sends digitized defect signals 43 to real time digital microprocessors 44. Microprocessors 44 use digitized signals 43 to determine if actual defects or strip 14 sweep (i.e., noise or movement) have been detected, and microprocessors 44 send actual defect detected signals 45 to PLC 28 and actual defect detected signals 47 to visualization system 46. PLC 28 then causes rejector 26 to discard defective razor blades.

Figure 2B:
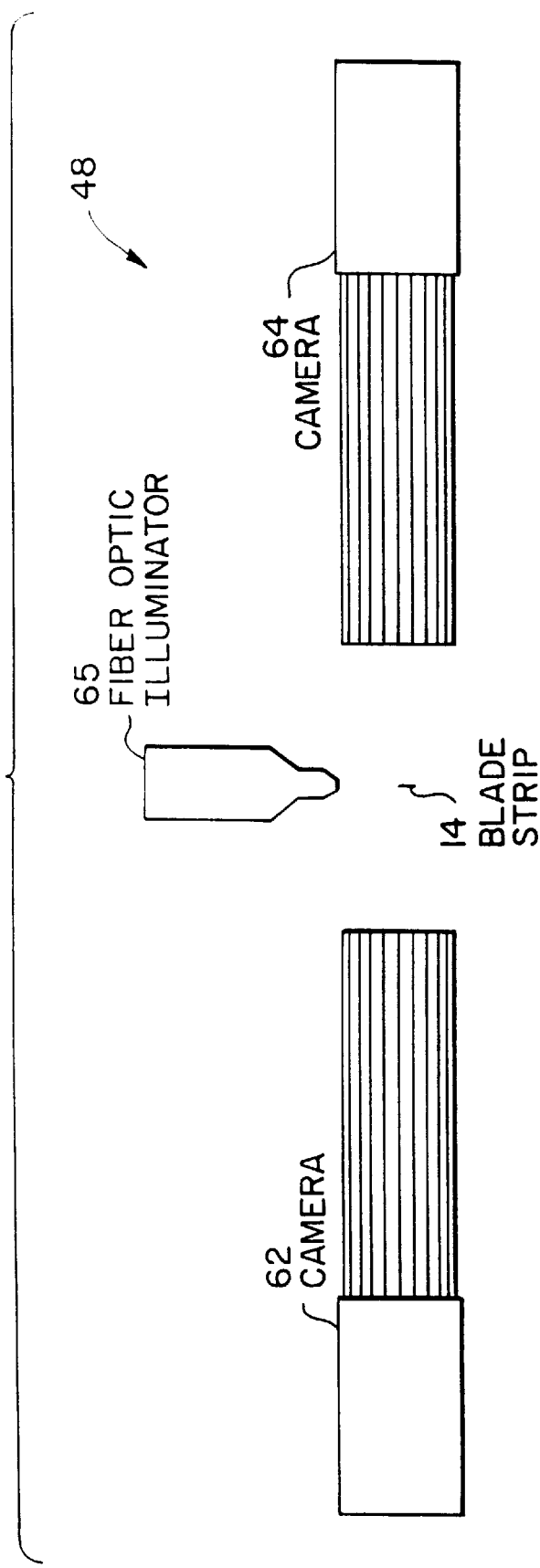
FIG. 2B shows a camera system.

Visualization system 46 controls a camera system 48 through which strip 14 passes downstream of the laser detectors 40. As seen in FIG. 2B, two cameras 62, 64 in camera system 48 take pictures of both sides of blade strip 14 using a fiber optic strobe illuminator 65. Visualization system 46 generates digitized images of the pictures taken by camera system 48, stamps the images with dates and times, and makes them available for display on operator interface 56 or for storage in storage system 58.

Visualization system 46 and storage system 58 may be connected to a factory-wide network and one or more operator interfaces 56 giving operators throughout the factory access to images and information about strip 14.

If microprocessors 44 indicate that an actual defect has been detected in strip 14, visualization system 46 determines, based on current strip speed, the arrival time downstream of the defect at a particular camera within camera system 48 and directs that camera to take a picture of the defect.

A picture of a defect taken in the blade strip before the razor blade is rejected may be more reliable than an image of the discarded blade, because the discarded blade may be further damaged in the process of being discarded.

Because the camera system 48 only operates at near video rates, the frequency at which images may be captured is limited. Only one image may be captured every fifty milliseconds. Thus, multiple defects detected within short distances of each other will not be imaged. As explained later, the visualization system implements a defect priority system for capturing images of the largest type of defect detected. Also, because the field of view of each image shows only 0.070 inches along the blade edge (just wider than a typical 100× microscope), the full extent of any damaged section may not be visible.

Visualization system 46 may direct camera system 48 to take pictures at predetermined intervals even when defects are not being detected. The information can be made available for display on operator interface 56 or for storage in storage system 58.

Visualization system 46 also controls a commercial laser micrometer 50 (FIG. 3) which measures the overall blade width of strip 14 and can be directed to take measurements periodically. Visualization system 46 analyzes these measurements and generates process trend charts. System 46 then makes the process trend charts and other information available for display on operator interface 56 and for storage in storage system 58 and over the factory network.

Inspector

Figure 3:
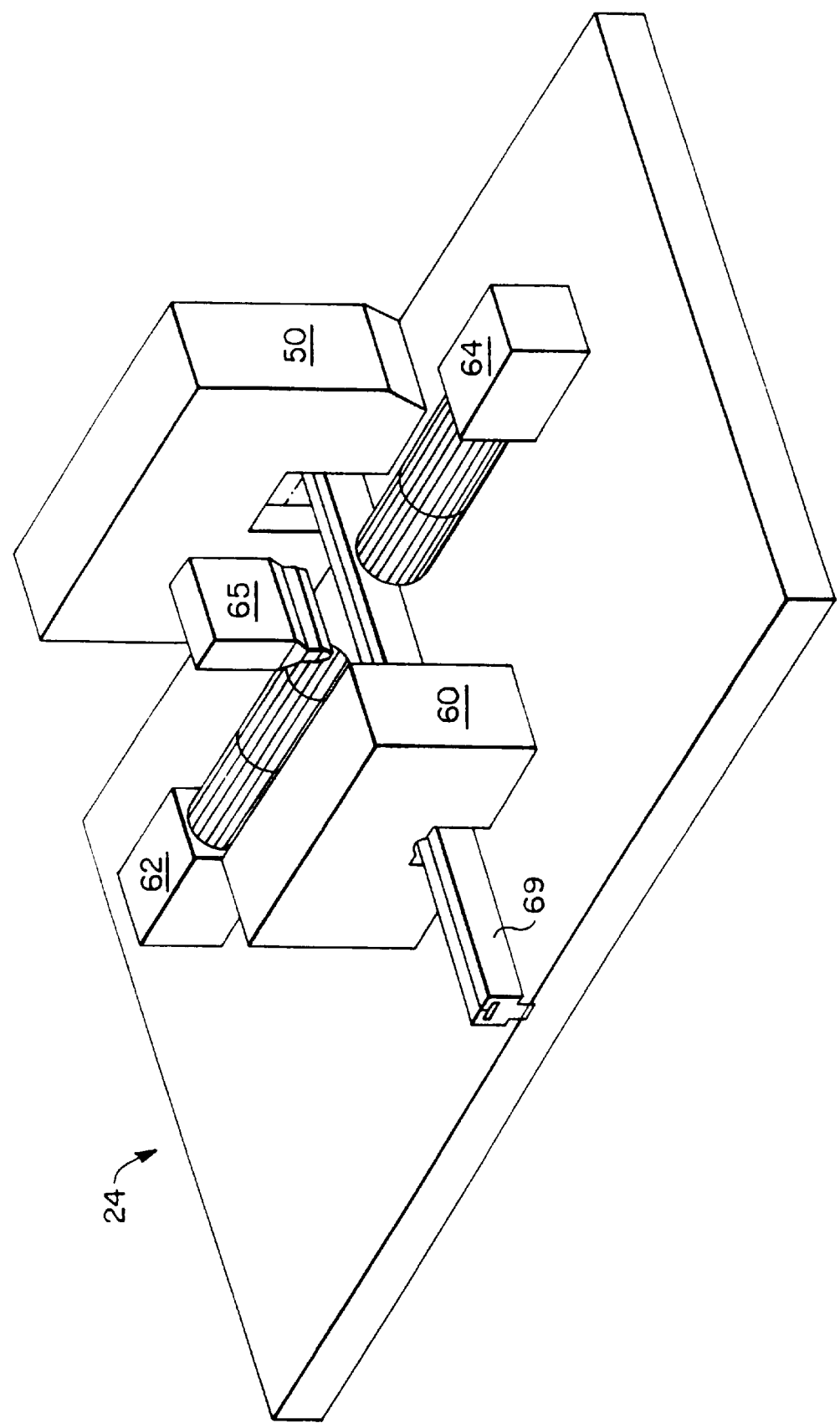
FIG. 3 shows a perspective view of an inspection system.

Referring to FIG. 3, inspector 24 includes detector housing 60 within which laser detectors 40 are mounted. Strip 14 passes through detector housing 60 and, thus, past laser detectors 40 before passing through camera system 48. Camera system 48 includes camera and lens 62, camera and lens 64, and light source 65. Light source 65 may be a fiber optic illuminator coupled to a strobe light. Strip 14 then passes through laser micrometer 50.

Figure 4:
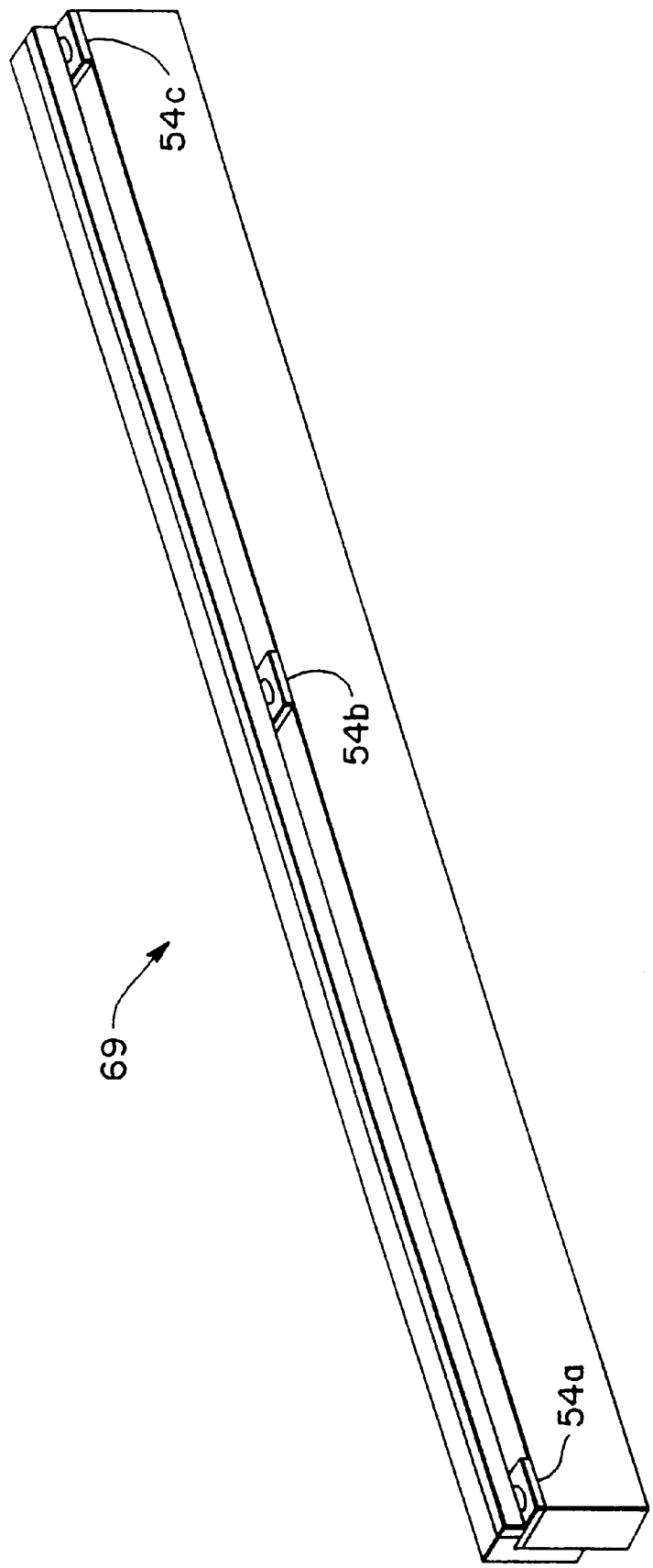
FIG. 4 shows a cross-sectional view of a magnetic guider.

While steel strip 14 passes through inspector 24, it rides in a magnetic guider 69 (FIG. 4) referenced against the bottom edge and one side of the strip. Three bottom lands 54a, 54b, 54c are spread over the path through inspector 24 (approximately fourteen inches). 54a is at the beginning of inspector 24, 54b is near the cameras, and 54c is at the end of inspector 24. In between the lands the magnetic guider is relieved to allow for strip sweep. The inspector is mounted midway between the lands to ensure even vertical motion of the strip.

Edge Detectors

Figure 5:
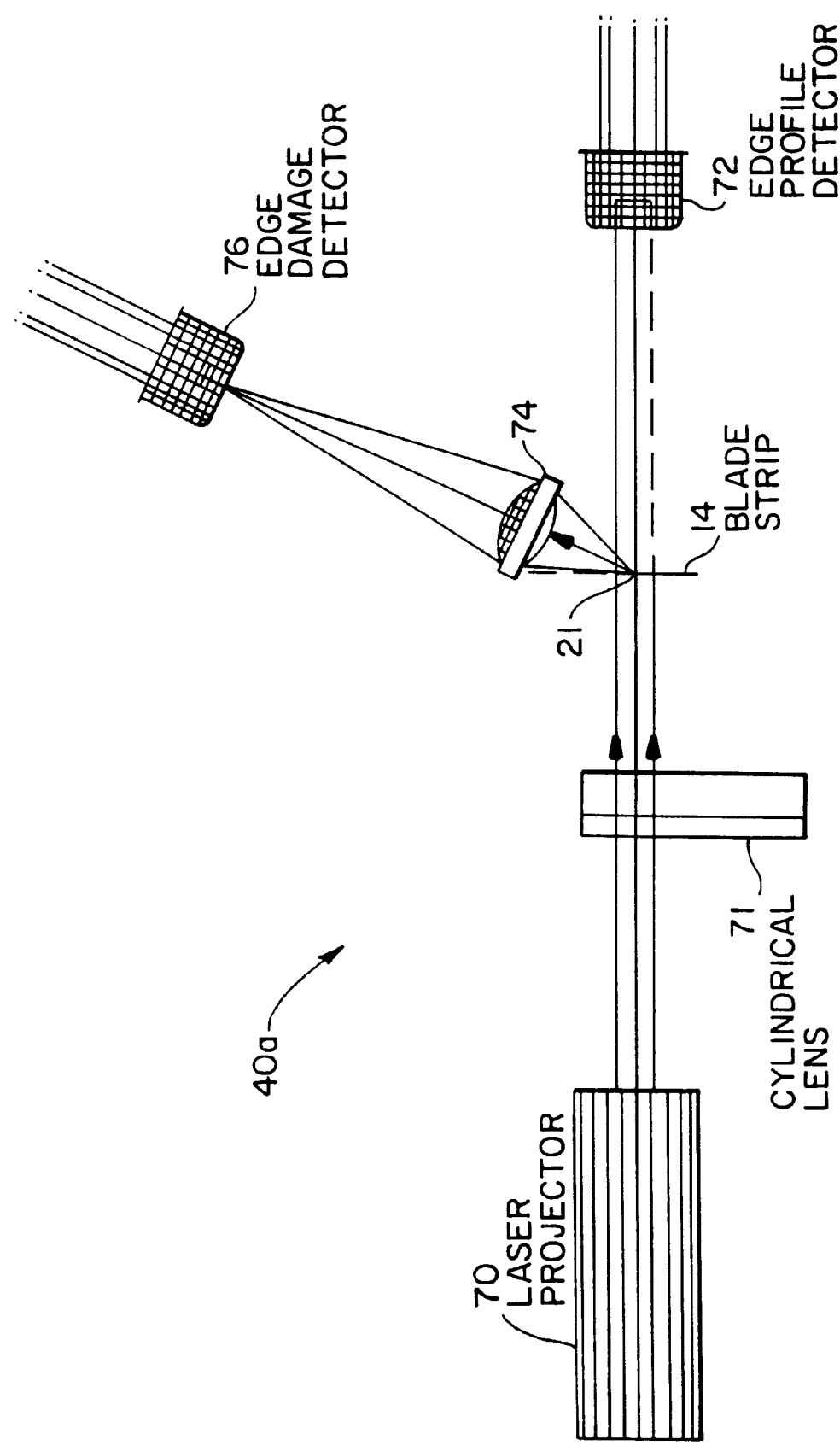
FIG. 5 shows a laser detector.

As seen in FIG. 5, one laser detector 40a includes a single commercial collimated diode laser projector 70 and a cylindrical lens 71 to focus laser beam into a line directed at the upper edge 21 of strip 14, which is shown traveling into FIG.

5. Edge profile detector 72 receives light passing over edge 21, and edge damage detector 76 receives light reflected from edge 21 and collected by lens 74. Edge damage detector 76 is located on the opposite side of a vertical line above edge 21 to prevent entry of laser light scattered from the illuminated side of strip 14.

Figure 6:
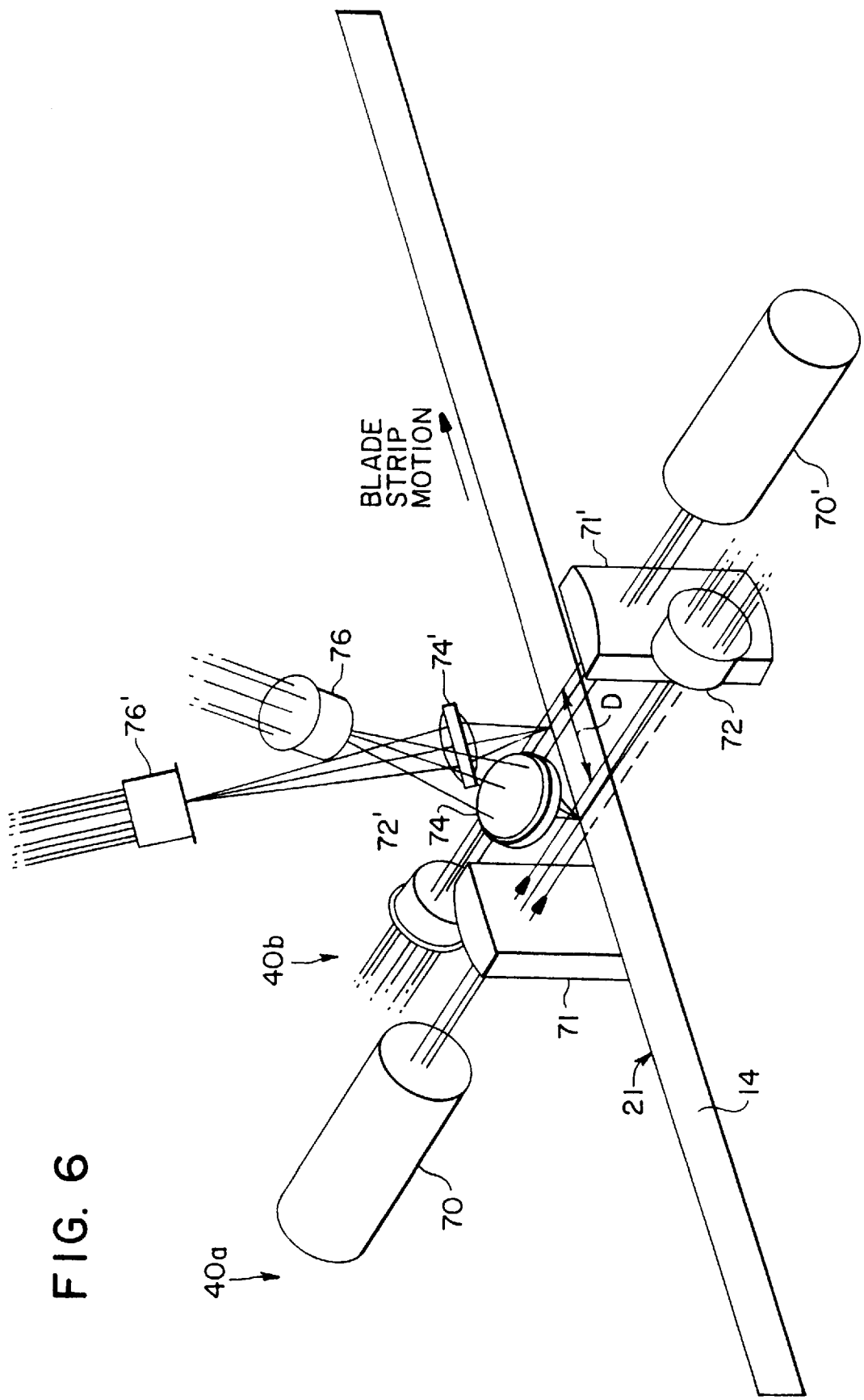
FIG. 6 shows a perspective view of an edge detector including two laser detectors.

A second laser detector 40b, shown in FIG. 6, is similar to detector 40a and includes a laser projector 70', cylindrical lens 71', edge profile detector 72', lens 74', and edge damage detector 76'. The elements of laser detector 40b, however, may be placed opposite to the elements of laser detector 40a. In this way the edge damage light reflected from either direction of edge 21 may be detected. Edge profile detectors 72 and 72' together are used to detect defects. Edge damage detectors 76, 76', and their respective lens 74, 74', are also used to independently detect defects. The two detectors 40a, 40b form a parallel set of laser detectors separated by a known small distance D of 0.2 inches in this example. The distance D is small enough to allow the two detectors to experience the same blade strip sweep perpendicular to the direction of machine motion and is large enough to be greater than the length of many defects that interrupt the edge.

Each edge profile detector 72, 72' generates a continuous analog profile signal. The profile signals from the detectors are then AC coupled, may be filtered, and are subtracted to provide a normalized edge profile signal. The normalized edge profile signal is digitally processed to discriminate real defects from process conditions, including blade sweep (i.e., noise or movement of the strip).

Figure 7:
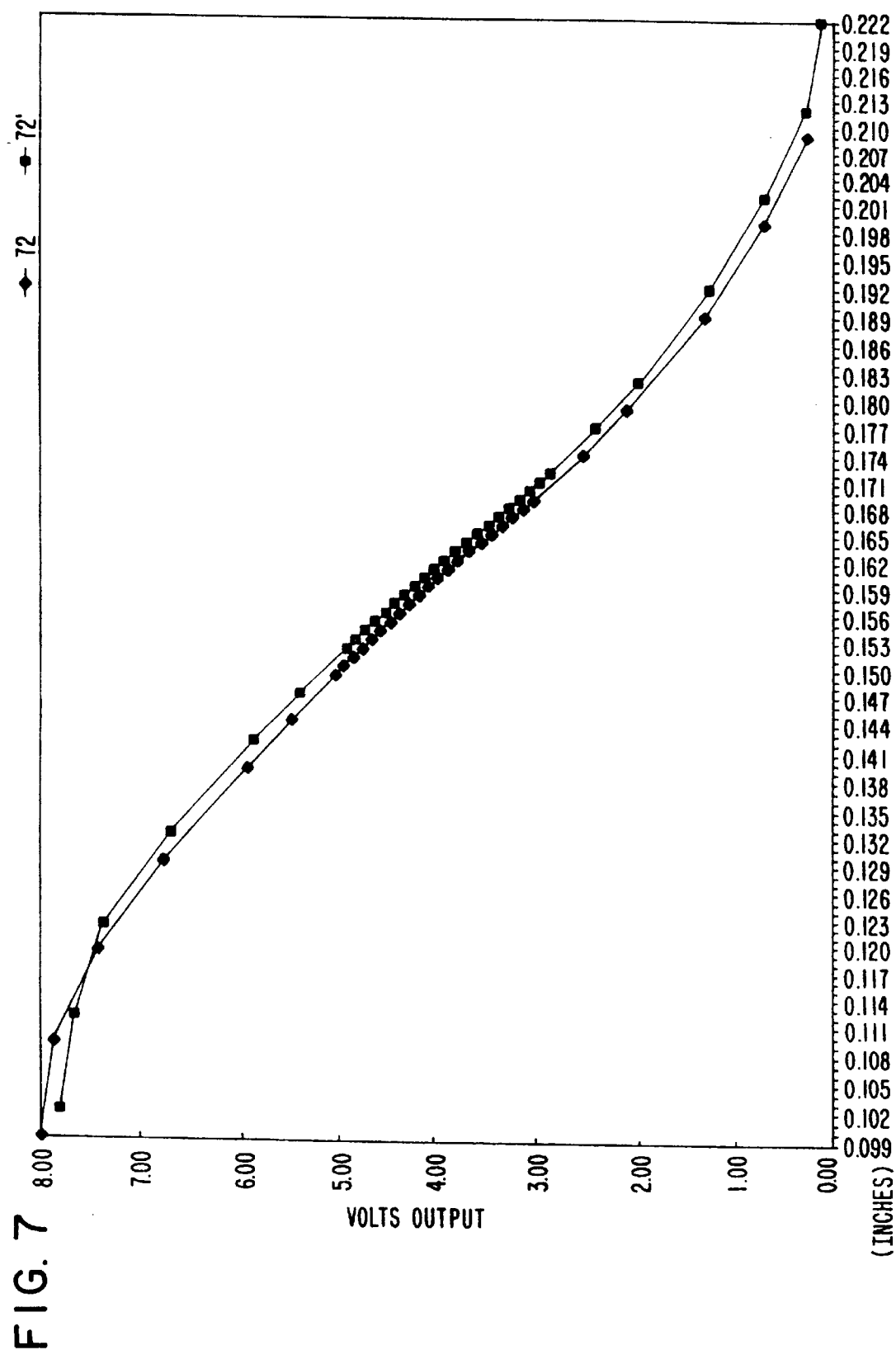
FIG. 7 shows a graphical representation of the edge profile signals generated by the laser detectors.

Edge 21, magnetic guider 69 and the laser projectors 70, 70' and detectors 72, 72' are aligned to use the center portion of the collimated laser beam, where the Gaussian beam profile is relatively flat. This gives a reasonably linear change in light with edge displacement, as shown in FIG. 7. Because the laser diode projectors emit elliptical collimated beams, the linear region in the long axis direction of the ellipse is reasonably large compared to the size of the sharpened edge of the blade strip. The usable linear range of approximately 0.03 inch (0.144 to 0.174) shown in FIG. 7 is enough to accommodate edge movement due to normal product variation and fixture stability in the magnetic guider.

Figure 8A:
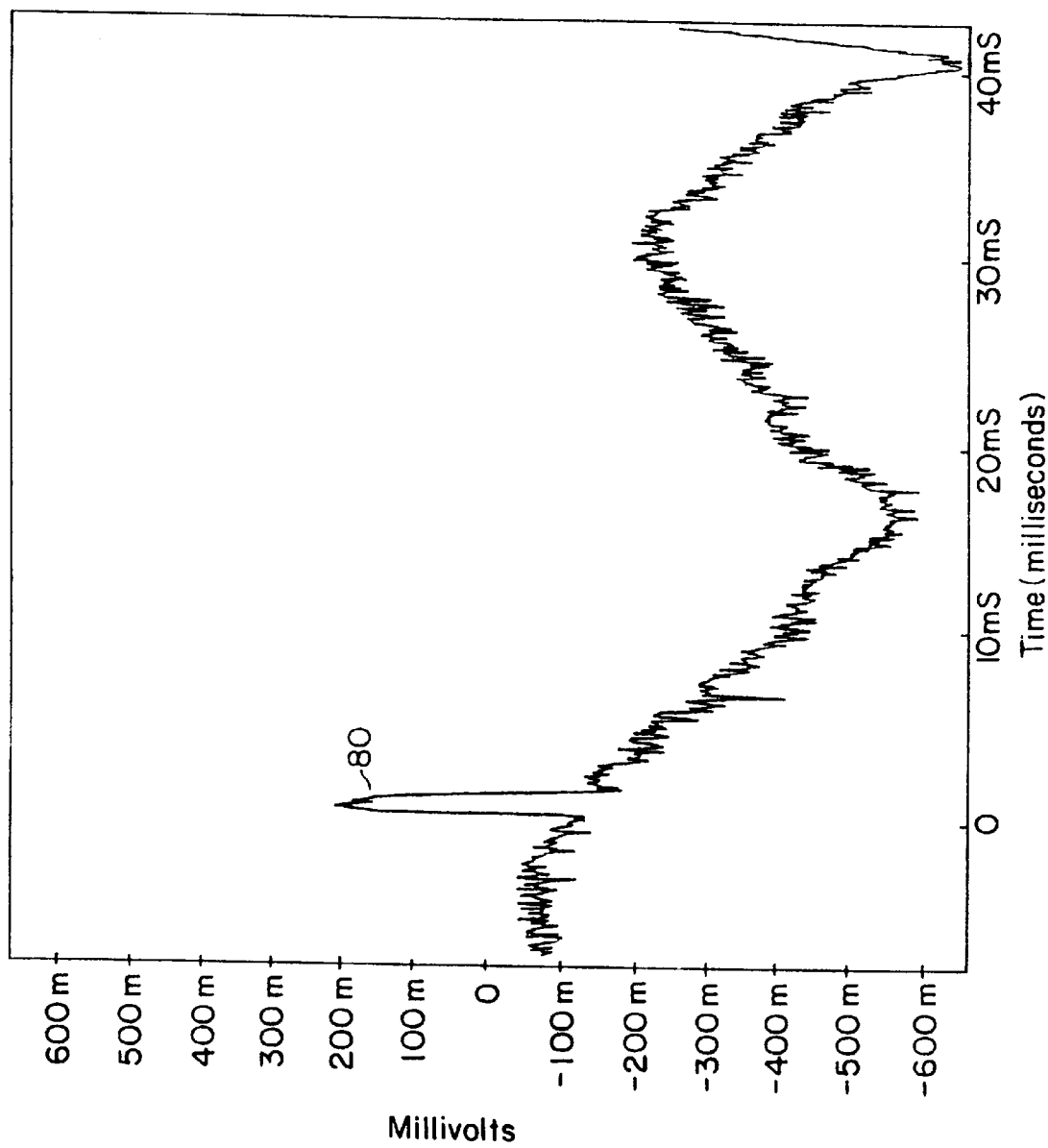
FIGS. 8A, 8B, and 8C show graphical representations of edge profile signals created by a defect.
Figure 8B:
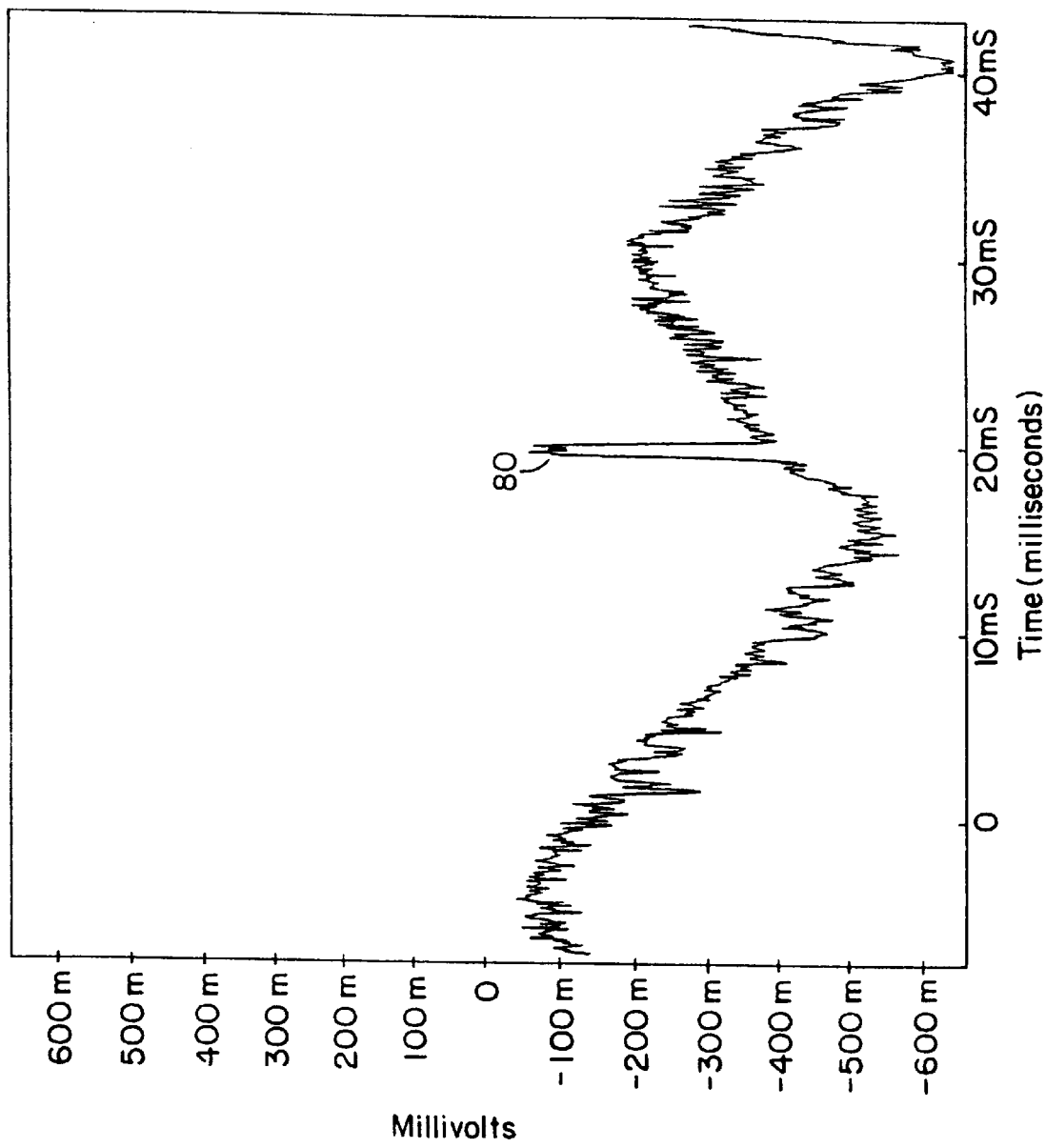

The subtracted signal from the leading and trailing edge profile detectors 72, 72' normalizes out most vibration in the strip 14, because the detectors 40a, 40b, are close together (about 0.2 inches apart) and see the same strip motion. Similarly, typical product variation in edge 21 occurs slowly (with a longer spatial wavelength) relative to the detector spacing and is also subtracted out of the combined signal. Edge discontinuities, however, sequentially pass both detectors and appear in the subtracted signal. FIGS. 8A and 8B respectively show a sample of the signal trace of an edge profile signal with an edge discontinuity 80 passing the lead edge profile detector 72 and the same edge discontinuity 80 passing the trailing edge profile detector 72'.

Figure 8C:
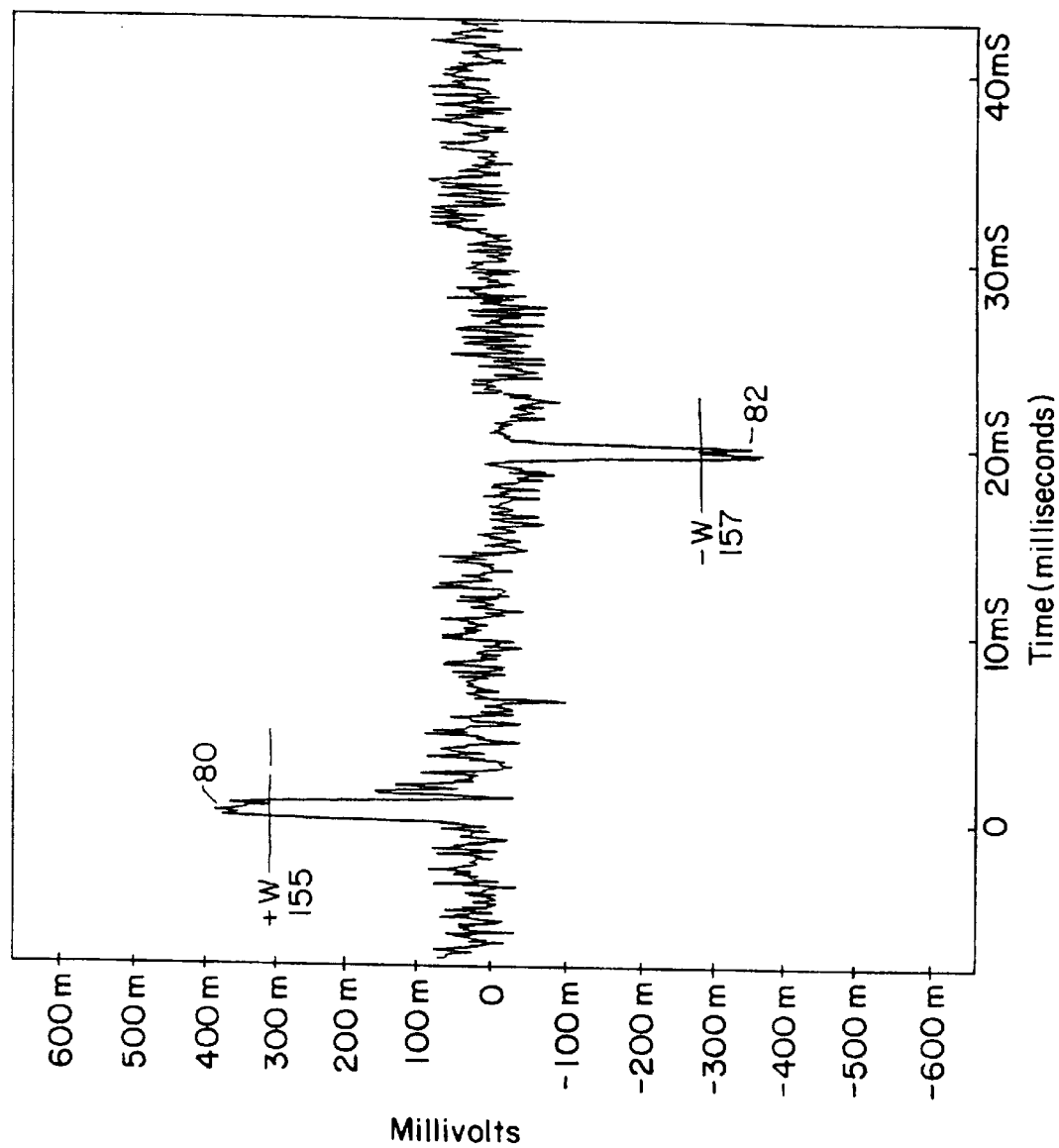

FIG. 8C dramatizes the characteristic appearance of a normalized discontinuity signature. Two features 81, 82 are generated in the normalized signal, one positive 81, and the other negative 82. These peaks are detected with window thresholds +W and −W on the signal. The size of W may be set appropriately for different types of defects. Excessive strip vibration or edge variations may exceed inspector signal thresholds but will not exhibit the characteristic inverted peaks 81, 82. Since both the strip speed and the detector spacing are known, any detected peak must have a corresponding peak of opposite polarity within a certain window of time to be an edge defect.

Additional defect discrimination from edge vibration and variations is obtained with time domain filtering of the signal before normalization. This reduces any random signal components outside of the filter passbands that would not appear simultaneously on both detectors, and also prevents high frequency artifacts from being generated if the signals were otherwise subtracted. For our application, window thresholds of 0.006 inches are used on the normalized signal with no filtering, thresholds of 0.0008 inches on the signal with a frequency response above 400 hz, and 0.0003 inches on the signal with frequency response above 1 Khz.

As shown in FIG. 9, analog electronic circuit 42 include four channels, each for detecting a particular kind of defect. The four channels continuously receive signals from laser detectors 40. Some defects may be detected by using both leading and trailing edge profile detectors, 72, 72'. Consequently, detector circuit 98 and detector circuit 102 receive signals 90, 90' from the leading and trailing edge profile detectors. Other defects may be detected based on leading edge damage detector 76 or on trailing edge damage detectors 76'. As a result, detector circuit 104 receives signals 94, 96 from edge damage detectors 76, 76', respectively.

Real time digital microprocessors 44 of inspector 24 (FIG. 2A) include four single board computers (SBC), SBC1 112, SBC2 116, SBC3 122, and SBC6 117 that receive defect signals from the analog detector channels and determine whether indicated defects are actual defects by determining whether defect criteria are met. Detector channel 98 sends signals 108 and 110 indicating one kind of defect to SBC1. Detector channel 102 sends signals 114 and 116, indicating a second kind of defect, to SBC6. Detector channel 103 sends signals 97 and 99 indicating a third kind of defect to SBC2. Similarly, detector channel 104 sends signal 118, indicating a fourth kind of defect and signal 120, indicating a fifth kind of defect, to SBC3.

When SBC1 determines that a defect exists, it sends defect signals 124, 125 and/or defect signals 126, 127 to image timing SBC4 130 and PLC 28, respectively. When SBC2 determines that a defect exists, it sends defect signals 128, 129 to image timing SBC4 130 and PLC 28, respectively. When SBC3 determines that a defect exists, it sends defect signals 131, 133 to image timing SBC4 130 and PLC 28, respectively. When SBC6 determines a defect exists, it sends defect signals, 132, 134 to image timing SBC4 130 and PLC 28, respectively. Visualization system 46 includes image timing SBC4 130. It determines when the defective portions of strip 14 reach camera system 48 and cause camera system 48 to take pictures accordingly. PLC 28 causes rejector 26 to discard defective razor blades.

A commercial thru-beam photodetector 202 is mounted to the rejector, detecting that the blades actually were rejected. This failsafe signal is monitored by SBC5 204, which also receives the original reject signals. SBC5 204 determines that all defects were actually rejected, and signals the PLC to stop the machine if they were not ejected.

Figure 10:
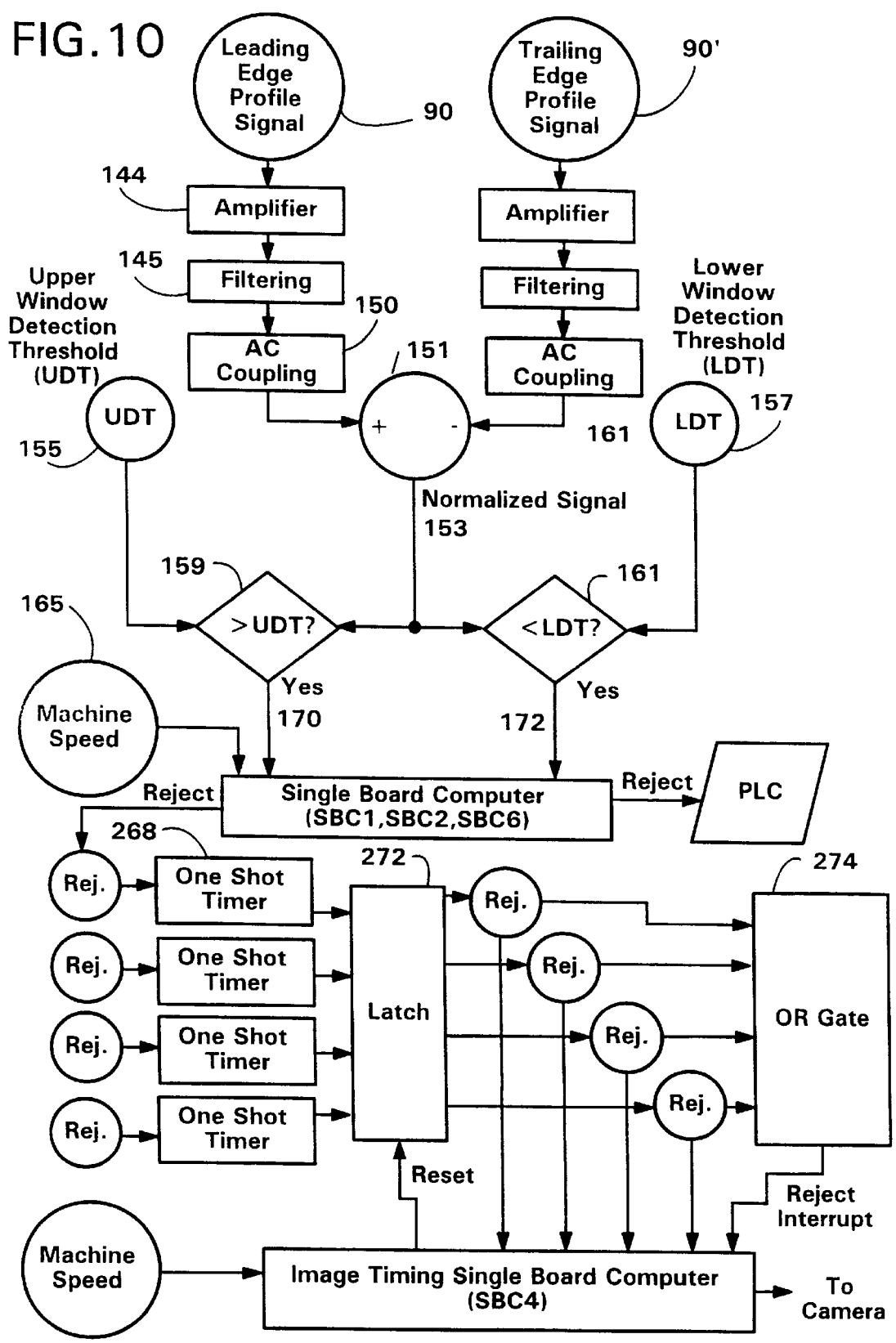
FIG. 10 shows a flow chart depicting the operation of an analog circuit (PCB), a single board SBC 1, 2, or 6 computer, and an image timing single board computer.

The flow chart of FIG. 10 depicts the operation of each of the large, medium, and small defect detector circuitry. The leading edge profile signal 90 is generated by the leading edge profile detector, and passed to a gain amplifier 144. The signals are then time domain filtered 145 for the medium and small defect circuits; the large defect circuit does no filtering, the medium defect circuit permits signals above 400 hz to pass, and the small defect circuit permits signals above 1 Khz to pass. The signals are then AC coupled 150 to remove any DC level offsets. The trailing edge profile detector signal 72' follows identical paths for the large, medium, and small defect circuits. The leading and trailing edge profile signals are then subtracted 151 to yield the normalized signal 153 for each of the large, medium, and small defect circuits.

The normalized signal is then compared 159, 161 with upper and lower window detection thresholds 155, 157 for each of the large, medium, and small defect circuits. When the normalized signal exceeds the upper threshold positively, output 170 to the SBC 163 is energized for the duration of the condition. When the normalized signal exceeds the lower threshold negatively, another output 172 to the SBC is energized for the duration of the condition. The upper and lower detection thresholds are set to ±0.006 inches (equivalent in voltage) for the large defect circuit, ±0.0008 inches for the medium defect circuit, and ±0.0003 inches for the small defect circuit. SBC1 receives the resulting signal from the large defect circuit, SBC6 receives the resulting signal from the medium defect circuit, and SBC2 receives the signal from the small defect circuit.

As described above, the single board computers determine whether defect signals represent actual defects by determining whether certain defect criteria are met. The single board computers each receive an input of sharpening machine line speed 165 from a commercial counter. Since the defect will pass the leading and trailing detectors with a time difference dependent on the line speed, each defect must generate corresponding defect signals through the upper and lower threshold comparators at a time difference proportional to the line speed and detector spacing (of 0.2 inches in this example). If the defect is torn out from the blade strip edge the light reaching the edge profile detectors 72, 72' will increase, and, it will first generate an upper threshold signal followed by a corresponding lower threshold signal; likewise, if the defect protrudes from the blade strip edge, the light reaching the edge profile detectors will decrease, and it will first generate a lower threshold signal followed by a corresponding upper threshold signal. Any threshold signal that stands alone without a following opposite threshold signal at the corresponding time is not from a defect, but rather from random blade strip motion or sweep.

Figure 11:
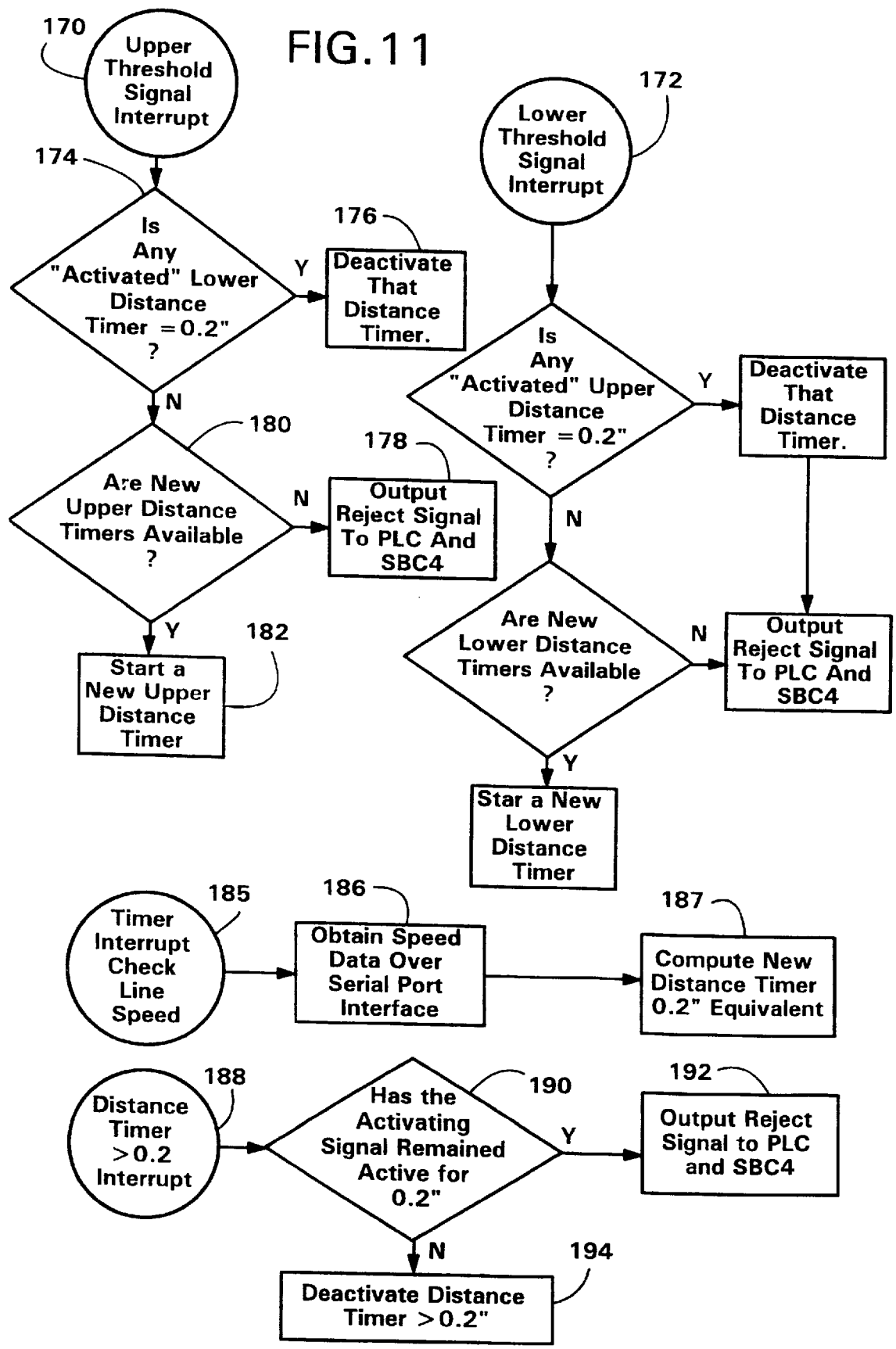
FIG. 11 shows a flow chart depicting the detection of an actual defect on a single board computer.

Referring to FIG. 11, the upper and lower threshold signals 170, 172 generate interrupts to SBC1, SBC2, and SBC6, which execute similar programs. An upper threshold signal interrupt will cause the program to check 174 for any timer activated by the lower threshold signal interrupt 0.2 inches earlier. If found, a defect has been detected and that timer will be deactivated 176 and a reject signal output 178 to the PLC 28 and image timing SBC4 130. The 0.2 inch timing must be valid to within some tolerance to generate a reject decision, ±15% being a reasonable level.

If no activated timers equal 0.2 inches±15%, then the program attempts to start 180 a new upper threshold signal timer (four are available in the embodiment program). If all four timers are in use, then the threshold signals must be coming in at too fast a pace, and a reject signal 178 is output. Otherwise, a new upper distance timer is started 182. The program works similarly for lower threshold signal interrupts. SBC1, SBC2, and SBC6 also have internal timer interrupts 185 to check the sharpening line speed from the commercial counter. The speed is checked 186 and updated several (e.g., four) times a second, and new distance timer limits are computed 187 for the 0.2 inch±15% values based on the most current line speed.

When any distance timer exceeds 0.2 inch+15%, it generates a program interrupt 188. The program then checks 190 whether the upper or lower signal that activated that timer remained continuously active over the 0.2 inch 15% duration. If that is the case, it was caused by a defect longer than the 0.2 inch detector spacing on the sharpening line, so that the leading edge of the defect passed both detectors before the trailing edge reached the leading detector. Therefore, a reject signal is generated 192. Otherwise, that distance timer is deactivated 194.

Figure 12:
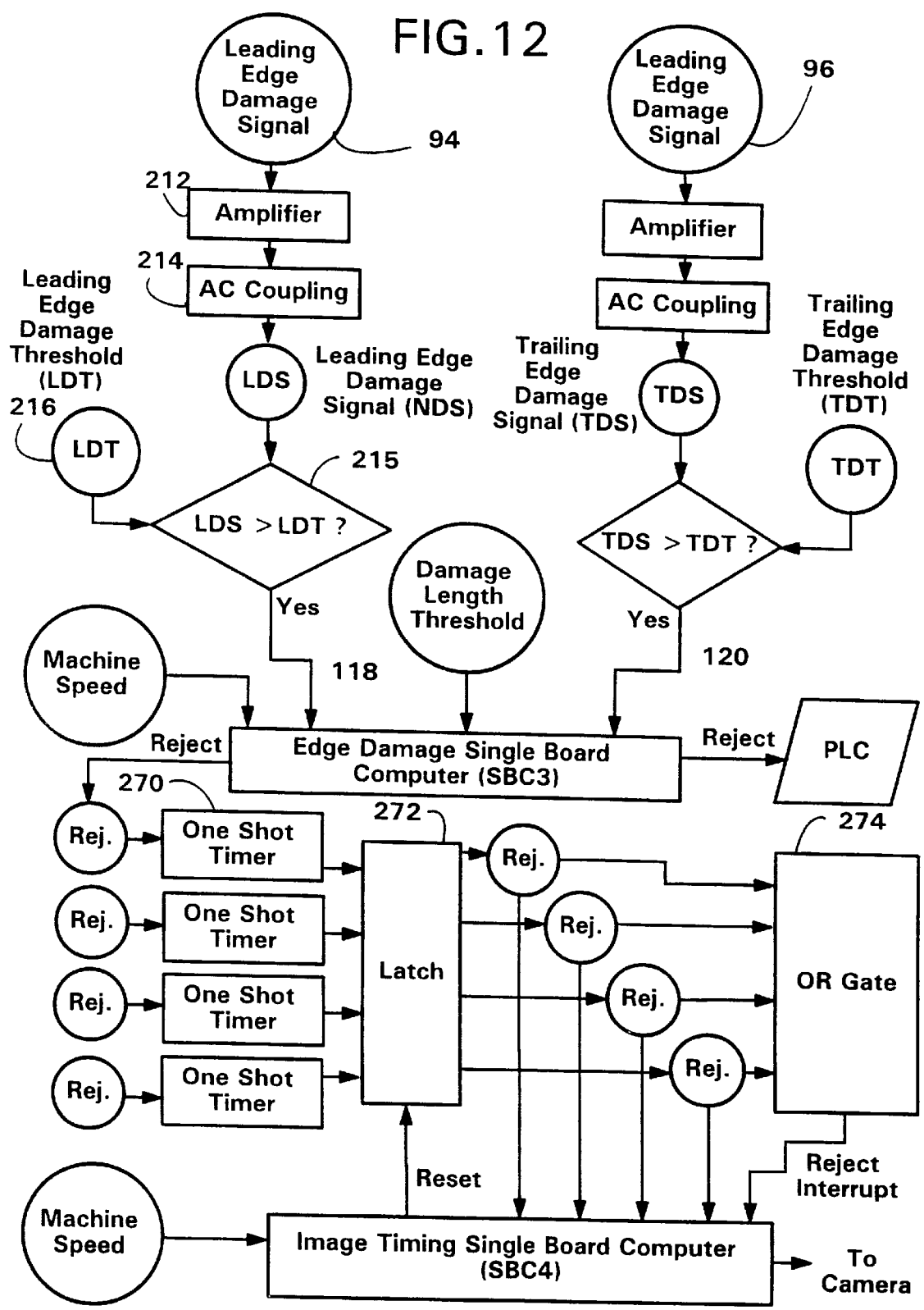
FIG. 12 shows a flow chart depicting the operation of an analog circuit detecting edge damage and a single board computer.

FIG. 12 depicts the operation of the edge damage defect detector circuitry. The leading edge damage signal 94 is generated by the leading edge damage detector and passed to a gain amplifier 212. The signal is then AC coupled 214 to remove any DC offsets. The signal is then compared 215 to a leading edge damage threshold 216, and output to the edge damage SBC3 218 is energized for the duration of the condition when it exceeds the threshold. The trailing edge damage signal follows an identical path.

Figure 13:
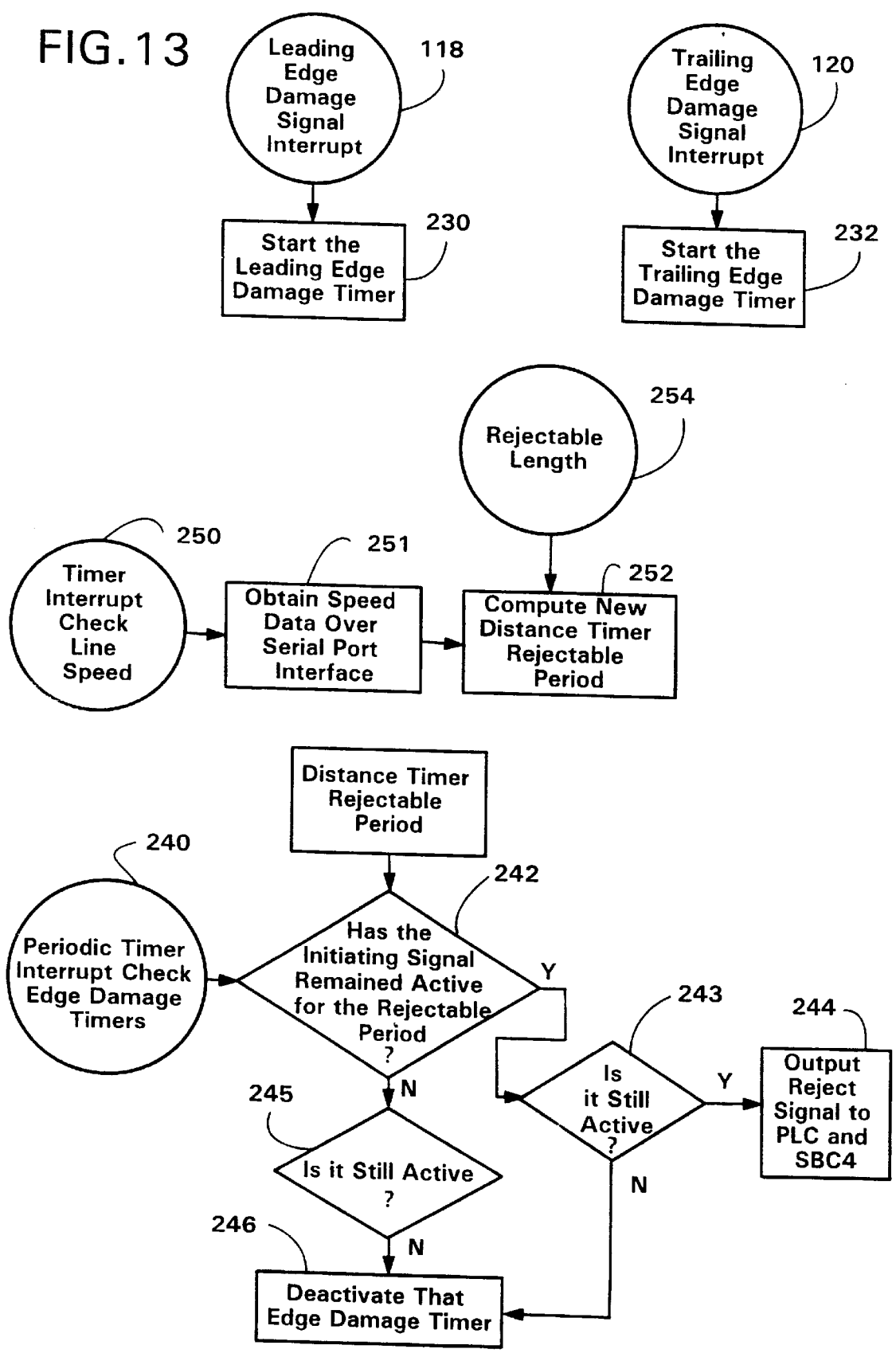
FIG. 13 shows a flow chart depicting the operation of a single board computer analyzing edge damage.

Referring to FIG. 13, the leading and trailing edge damage signals 118, 120 that exceed the thresholds generate interrupts to SBC3 122. These signals will cause the program to start leading or trailing edge damage timers 230, 232. A periodic timer interrupt 240 will cause the program to check 242 each edge damage timer to determine if the initiating signal has remained active for the rejectable period. If it has, a reject signal is output 244. If the edge damage signal continues to be asserted 243, then the reject signal is output repeatedly. If, however, the edge damage signal expired before the rejectable period was fulfilled 245, then that edge damage timer is deactivated 246.

As in SBC1, 2, and 6 on FIG. 11, this program also has a periodic internal timer interrupt to check 250 line speed from the commercial counter. The speed information is obtained 251 and used to compute 252 a rejectable period equivalent to the rejectable edge damage length 254. SBC3 122 receives the input of rejectable length 254 from user selectable switches (the minimum continuous edge damage length that is considered rejectable).

Figure 14:
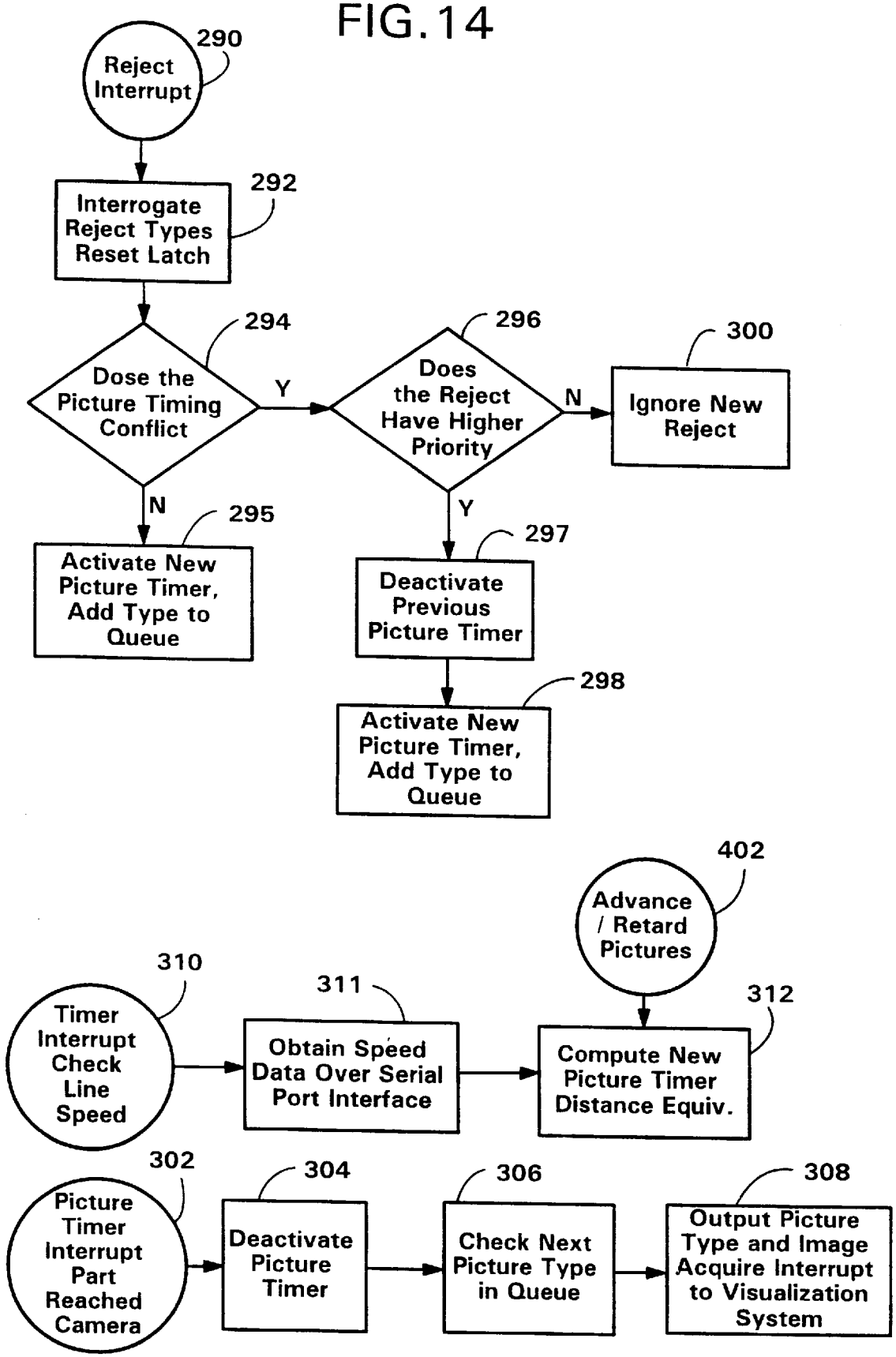
FIG. 14 shows a flow chart depicting the operation of an image timing single board computer.

If SBC1, SBC2, SBC3, or SBC6 determines that an actual defect has been detected, then they assert signals to the PLC 28 to reject the defective blade, and to image timing SBC4 130. Referring to FIG. 10 and FIG. 14, SBC4 130 receives the defect detected signals through one shot timers (268 being among them) and latches 272 (being among them), and the signal notification through an OR gate 274. Since more than one defect detection channel may be energized by any particular blade strip defect, SBC4 130 uses the latched signal presentations to choose the largest defect type for imaging display. This guarantees that the defect displayed is categorized with the proper reject type.

Referring to FIG. 14, SBC4 130 receives the ORed reject interrupt signal 290, and then interrogates 292 the reject types and resets the latched signals. Since the imaging is constrained by video rates as explained earlier, SBC4 determines 294 if a picture timing conflict will occur with a defect picture previously in the queue. If no conflict exists, then a picture timer is activated 295 and the picture type (large, medium, etc. defect) is added to the queue. If a conflict exists, the program compares the new defect picture type priority to the previous picture 296, with larger defects having the higher priority. If the new picture is of a higher priority, then the previous picture timer is deactivated 297, and a new picture timer is begun 298 with the new picture type placed in the queue. Otherwise, if the new picture is of lower priority, it is ignored 300. This process is similar to the logic employed to choose the largest reject picture type from among the latched signal presentations to SBC4 130.

When the picture timer reaches the preset distance equivalent to place the defect in front of the cameras, it generates an interrupt 302. The program then deactivates that timer 304, checks 306 the picture type in the queue, and outputs 308 the information to the visualization system. The visualization system 46 then acquires the image using the appropriate camera and strobe illumination, stores the image to digital memory, and labels the image with the picture type, date, and time information.

As in the other SBCs, this program also has a periodic internal timer interrupt 310 to check line speed from the commercial counter. The speed information is obtained 311 and used to compute 312 the picture timer period equivalent to the distance from the reject of the sensor to the camera. SBC4 also receives a user selectable input 402 from the visualization system to advance or retard the picture timing, thereby shifting the centration of the defect in the resulting images.

Rejector

Once a defect is detected, the PLC 28 locates the defect to the blade in the strip immediately at the inspector 24. The entire blade is then considered defective. The PLC 28 tracks the blade down the sharpening line and through the cutter using blade-by-blade pulses from a commercial encoder mounted to the sharpening line. The defective blade is then segregated by a similar device to that used to strip blades from the cutter and magazine them. A commercial thru-beam photoelectric device monitors the presence of rejected blades that are segregated by the rejector. SBC5 204 (FIG. 9) receives the reject signals from SBC1, SBC2, SBC3, and SBC6, as well as the rejected blade presence from the thru-beam photodetector. SBC5 tracks the rejects through the sharpening line and the cutter and rejector using the blade-by-blade pulses from the sharpening line encoder. SBC5 acts as a failsafe system for the PLC and the rejector. Should the defective blades not be successfully rejected, SBC5 will signal the PLC to stop the sharpening machine.

Visualization System

The visualization system 46 may be a personal computer system containing a commercial imaging card, video camera and lens, and strobe light. The operator interface display is via a commercial touch screen VGA video monitor linked to the personal computer system. SBC4 130 triggers the visualization system 46 to capture an image when the defect detected in the blade strip has traveled down the sharpening line and is within the camera field of view (0.070 inch wide in this embodiment). Motion of the strip is frozen by the strobe light pulse to yield a clear defect image, which is displayed on the operator interface screen. Up to forty of the most recent defect images may be maintained in RAM memory on a 16 megabyte imaging board.

Figure 15:
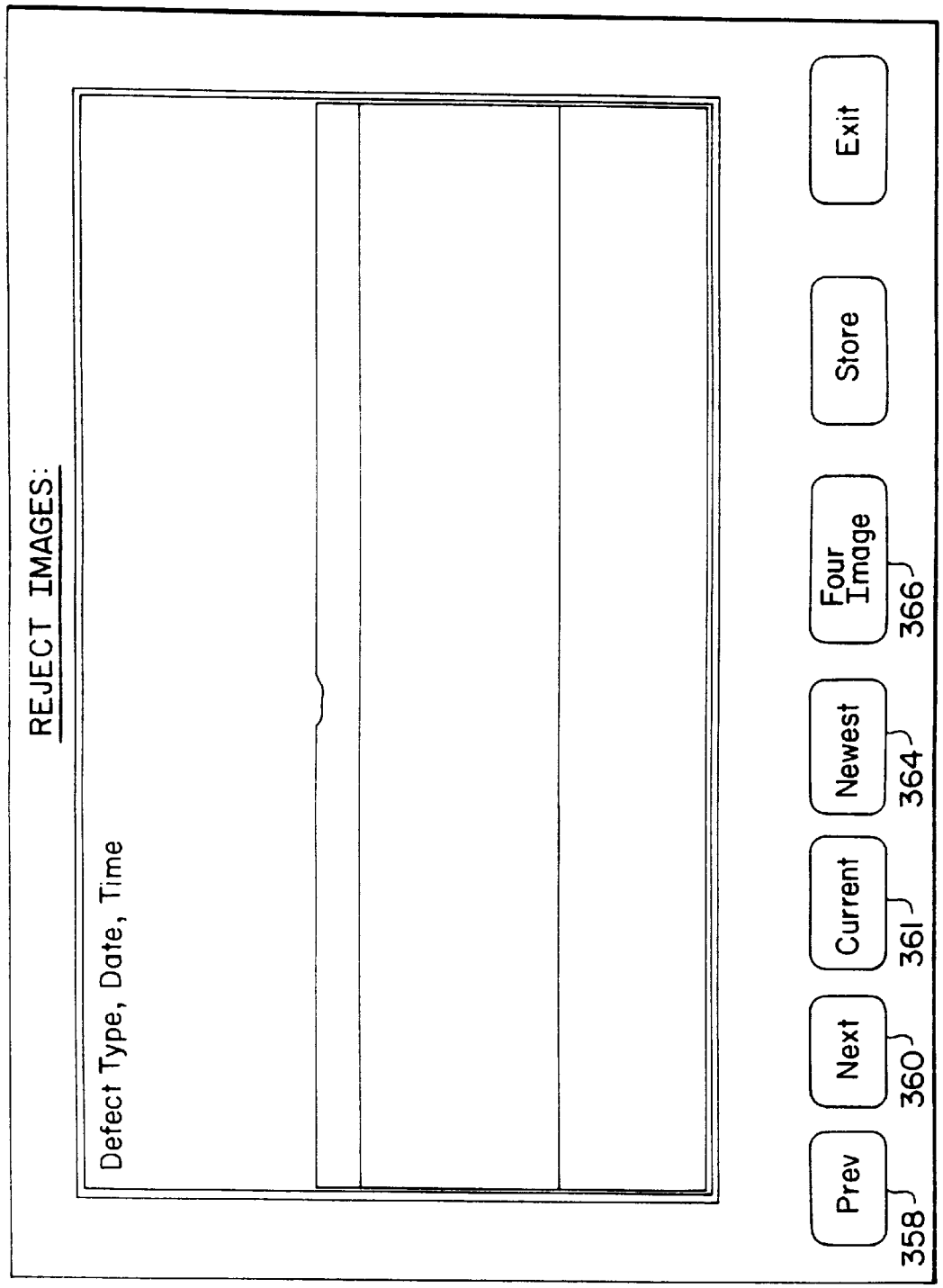
FIG. 15 shows a reject image screen.

An example of the operator interface reject imaging screen is shown in FIG. 15. This screen is initialized with the "switch type" button 357 set to NEWEST, causing the most recent defect image of any type to be updated to the screen display. The "switch type" button may be activated to cycle through the different defect categories, such as large, medium, small or edge damage defects.

A queue of the most recent images of each type of defect are stored in RAM memory. The image queue for each defect type may be scrolled through using the previous 358 or next buttons 360 once the switch type button 357 is used to select the defect type. The image selected will remain on the screen until it falls off the end of the queue of the most recent pictures for that defect. Activating the current button 361 will display the most recent image of the type selected.

Activating the four images button 364 causes visualization system 46 to divide the display screen into four quadrants and display one defect image in each quadrant. Activating the store button 366 causes visualization system 46 to write the displayed image to permanent storage 58 (FIG. 2A) on the local hard disk or on a network if the personal computer is connected to a network.

Trend Imaging

Figure 16:
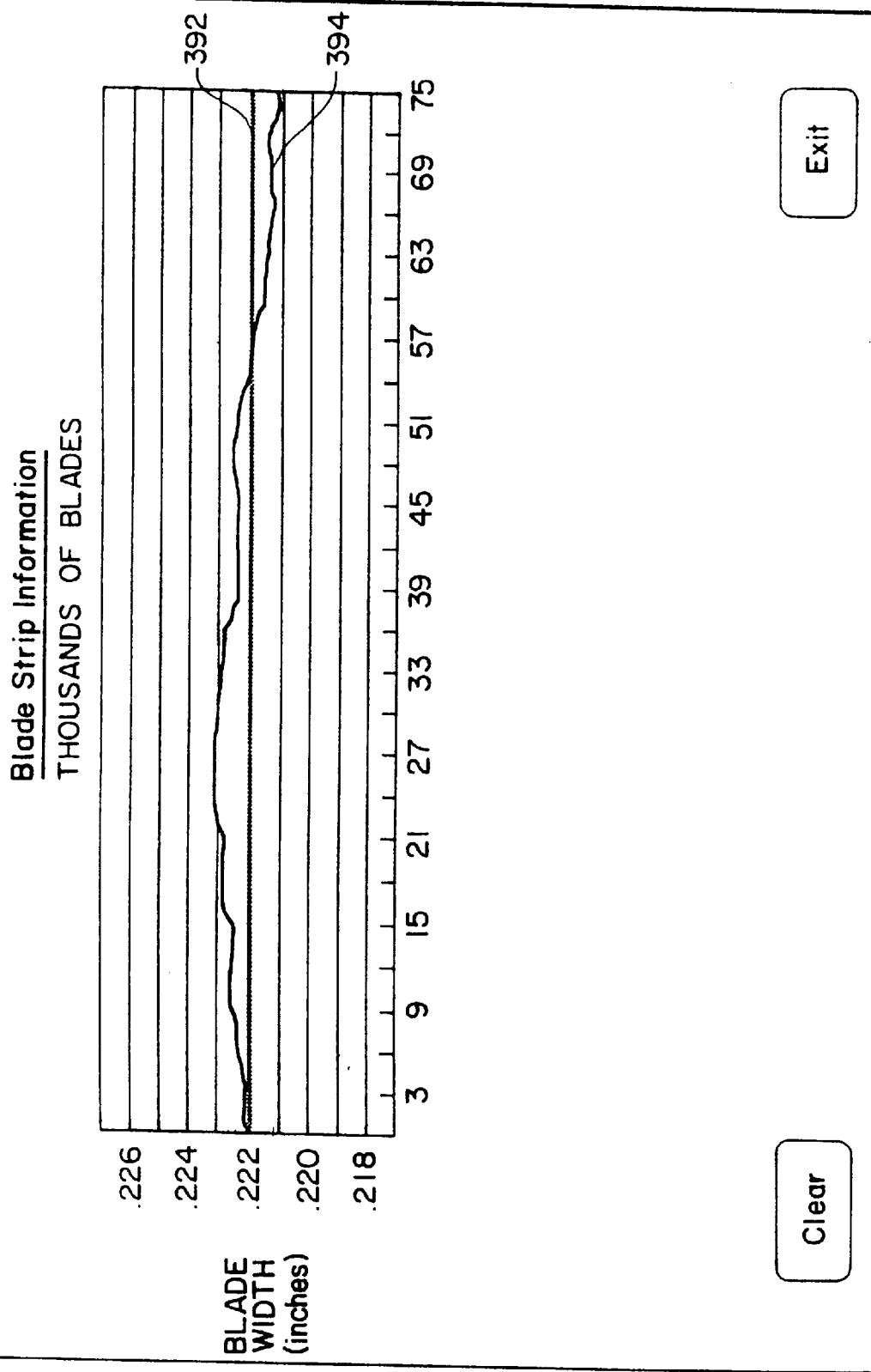
FIG. 16 shows a blade width trend analysis chart.

A trend screen may also be displayed on the visualization system as shown in FIG. 16. The plotted blade width information is measured by laser micrometer 50 which samples blade width data at a selectable rate. The data is then plotted on the graph shown and trend lines are drawn to connect the data points.

The target width 392 is shown on the graph and may be a different color than the actual strip width 394, and warnings may be automatically posted if strip width approaches predetermined limits.

Image Control

An image control screen may also be displayed on the visualization system as shown in FIG. 17. This screen allows the timing of image acquisition to be adjusted. By acquiring pictures a little bit earlier or later in time, the defects can be shifted to the left or right in the images displayed. By moving the time of image acquisition, evidence of process conditions that are causing defects (i.e., scratches, gouges, etc.) may be found. The slider control button 402 may be activated to either advance or retard the timing of the upcoming pictures in one quarter field of view increments. Maximum adjustment is nearly plus or minus two fields of view or plus or minus 0.174 inches.

Other embodiments are within the scope of the following claims.

What is claimed is:

1. A visualization system for razor blade manufacturing comprising an inspector that detects defects in the edge of a moving strip of razor blade material moving along a path, said inspector being located at a first, upstream position along said path, said inspector generating a defect signal when a defect is detected, said inspector including at least one beam directed perpendicular to the direction of movement of the strip of razor blade material, a camera for imaging an edge of said moving strip of razor blade material, said camera being independent of said inspector, said camera being located downstream of said inspector at a second, downstream position along said path along said moving strip, said camera being controlled to only take pictures of particular portions of said strip, said particular portions being fewer than all portions of said strip, said camera being responsive to said defect signal to take a picture of said strip at a predetermined time subsequent to said defect signal such that a picture is taken of said defect that had been detected at said inspector at the time that said defect passes said camera at said second, downstream position, a monitor, coupled to the camera, for displaying images of said defects captured by the camera, and a storage system, coupled to the camera and the monitor, for storing images of said defects captured by the camera, the monitor being capable of displaying the stored images of said defects.

2. The visualization system of claim 1 further comprising a light source directed at the edge of the strip;

and wherein said camera is a first camera and lens, in close proximity to the light source and on a first side of the strip, where the first camera and lens takes pictures of the edge of the strip as the strip passes the first camera and lens; and further comprising a second camera and lens, in close proximity to the light source and on a second side of the strip, where the second camera and lens takes pictures of the edge of the strip as the strip passes the second camera and lens; and a computer that receives pictures from the first and second cameras, generates digitized images of the pictures, and displays the digitized images on said monitor.

3. The visualization system of claim 2 wherein the computer receives the defect signal and causes the first camera and lens and the second camera and lens to take pictures of the strip at a predetermined time such that pictures are taken of detected defects.

4. The visualization system of claim 3, wherein the predetermined time is adjustable and wherein the computer includes an input device through which an operator can input timing adjustments to which the computer responds by causing the first camera and lens and the second camera and lens to take pictures of the strip at an adjusted predetermined time when defect signals are received.

5. The visualization system of claim 2, further comprising a storage system that stores the digitized images in response to instructions from the computer, and wherein an operator using an input device of the computer can cause the computer to retrieve stored digitized images from the storage system for display on the monitor.

6. The system of claim 1 wherein said inspector includes a pair of parallel, closely spaced laser beams.

7. A visualization system for razor blade manufacturing comprising an inspector that detects defects in the edge of a moving strip of razor blade material and generates a defect signal when a defect is detected, a camera for imaging an edge of said moving strip of razor blade material, said camera being located downstream of said inspector along said moving strip and responsive to said defect signal to take a picture of said strip at a predetermined time such that a picture is taken of said defect, a monitor, coupled to the camera, for displaying images captured by the camera, and a storage system, coupled to the camera and the monitor, for storing images captured by the camera, the monitor being capable of displaying the stored images wherein said inspector includes a pair of parallel, closely spaced laser beams, wherein the parallel laser beams include a first laser system including a first projector for projecting a first laser beam at the edge in a direction perpendicular to the direction of movement of the strip and perpendicular to the edge and a first profile detector for detecting a portion of the first laser beam passing over the edge and for generating a first signal representing the detected portion of the first laser beam; and a second laser system, in close proximity to the first laser system, including a second projector, for projecting a second laser beam at the edge in a direction perpendicular to the direction of movement of the strip and perpendicular to the cutting edge and a second profile detector for detecting a portion of the second laser beam passing over the edge and for generating a second signal representing the detected portion of the second laser beam.

8. The system of claim 7, further comprising:

a normalizing circuit that receives the first and second signals from the first and second profile detectors, substantially filters out movement of the edge, and generates an edge discontinuity signal; and a defect detection circuit that receives the edge discontinuity signal, processes the edge discontinuity signal to detect defects in the edge, and generates a defect signal in response to detected defects.

* * * * *